United States Patent [19]
Schraga

[11] Patent Number: 5,797,942
[45] Date of Patent: Aug. 25, 1998

[54] RE-USABLE END CAP FOR RE-USABLE LANCET DEVICES FOR REMOVING AND DISPOSING OF A CONTAMINATED LANCET

[76] Inventor: Steven Schraga, 9433 Byron Ave., Surfside, Fla. 33154

[21] Appl. No.: 716,748

[22] Filed: Sep. 23, 1996

[51] Int. Cl.$^6$ .................................. A61B 17/32
[52] U.S. Cl. .......................................... 606/182
[58] Field of Search .......................... 606/182, 183, 606/181; 604/263

[56] References Cited

U.S. PATENT DOCUMENTS

| | | | |
|---|---|---|---|
| 4,869,249 | 9/1989 | Crossman et al. | 606/182 |
| 5,074,872 | 12/1991 | Brown et al. | 606/182 |
| 5,207,699 | 5/1993 | Coe | 606/182 |
| 5,454,828 | 10/1995 | Schraga | 606/181 |

*Primary Examiner*—Michael H. Thaler
*Attorney, Agent, or Firm*—Malloy & Malloy, P.A.

[57] ABSTRACT

An improved and re-useable end cap for use with common, hand-held lancet devices, of the type having a main body and an actuatable lancet receiving assembly structured to temporarily hold a lancet inserted thereinto and to drive the lancet into a piercing orientation so as to prick a patient's skin. The re-useable end cap of the present invention includes a housing having a first end defining an open mouth for removable attachment to the lancet device, a second end having an opening therein and defining a tubular, hollow, main body between therebetween. The open mouth and main body of the cap are structured and disposed to permit at least partial passage of the lancet and lancet receiving assembly therethrough and into a piercing orientation wherein a sharp tip of said lancet is exposed through the opening of the second cap end. The improved re-usable end cap of the present invention, which are intended for use after the lancet receiving assembly has been fired, includes at least one member attached to the cap housing which is movable relative to the cap between a first withdrawn position and a second engaged position. In the second engaged position, the at least one member attached to the cap housing engages the lancet so as to withdraw the lancet from the lancet receiving assembly upon removal of the end cap from the lancet device, and can be utilized to selectively retain the lancet within the cap to facilitate proper disposal.

20 Claims, 3 Drawing Sheets

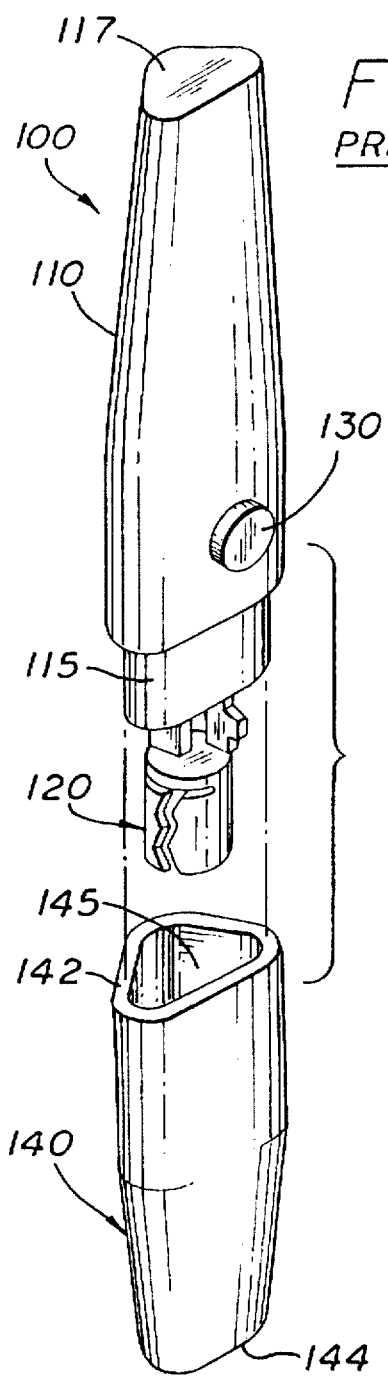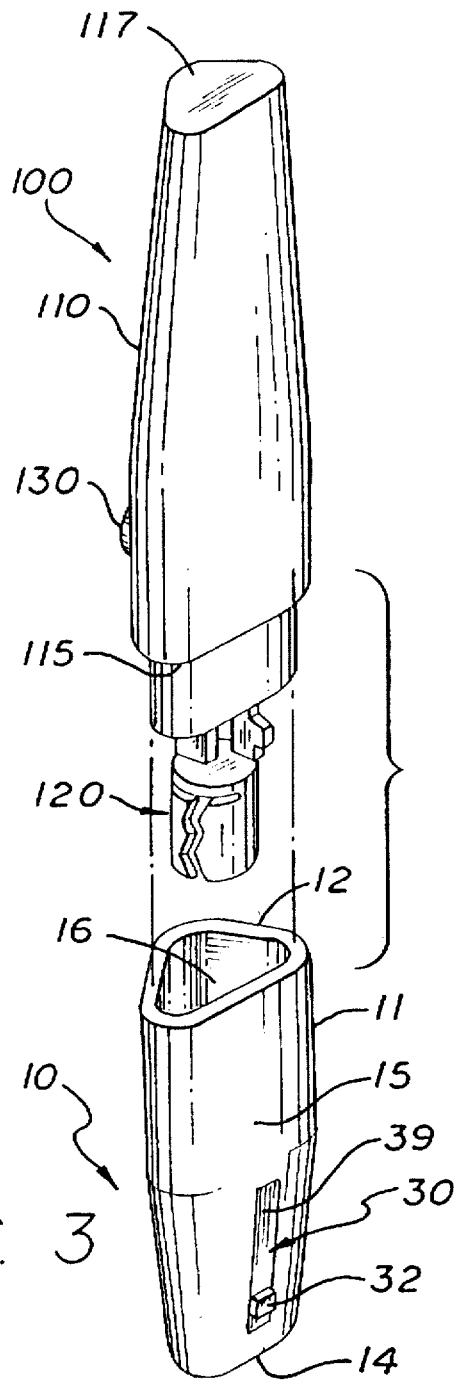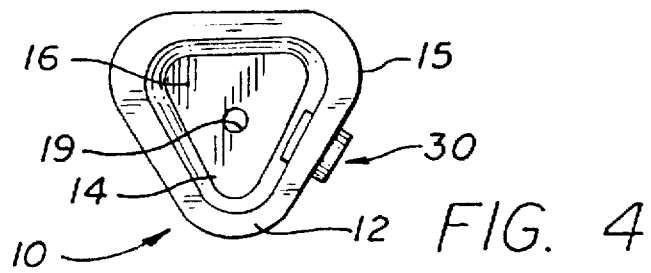

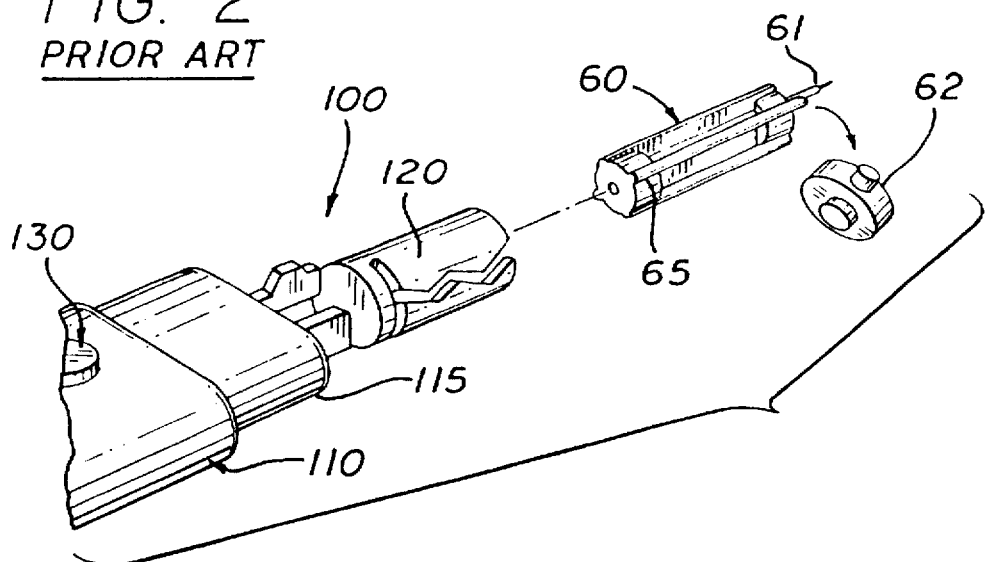
FIG. 2 PRIOR ART
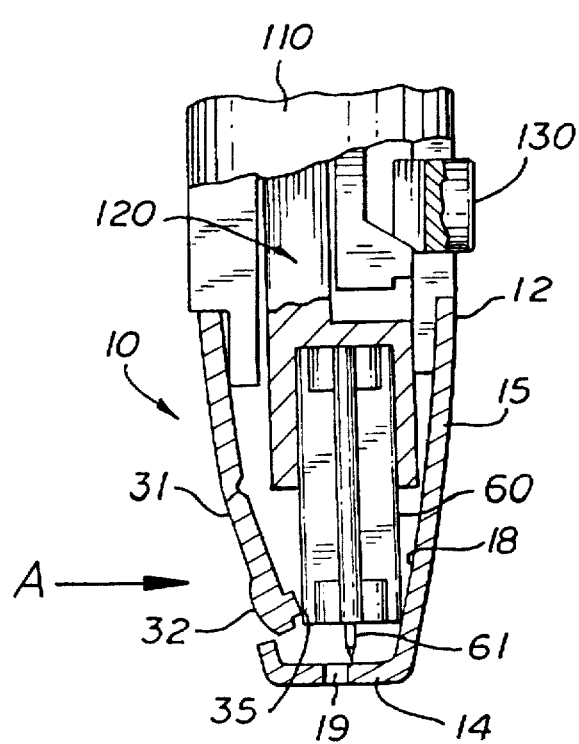
FIG. 5-A
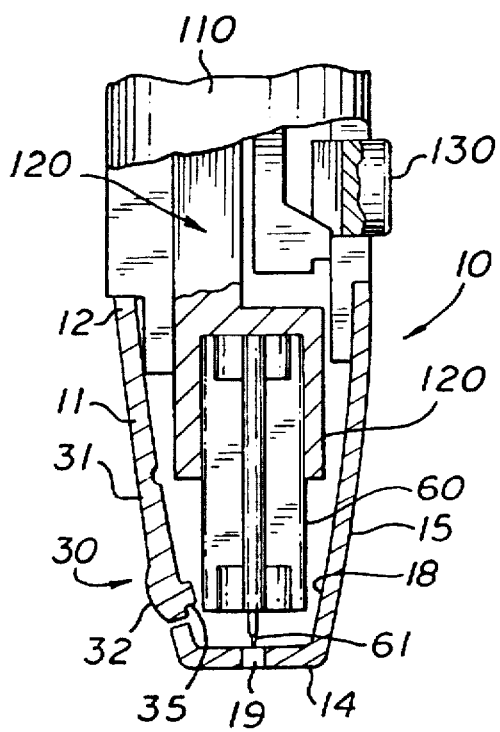
FIG. 5-B

FIG. 6-A
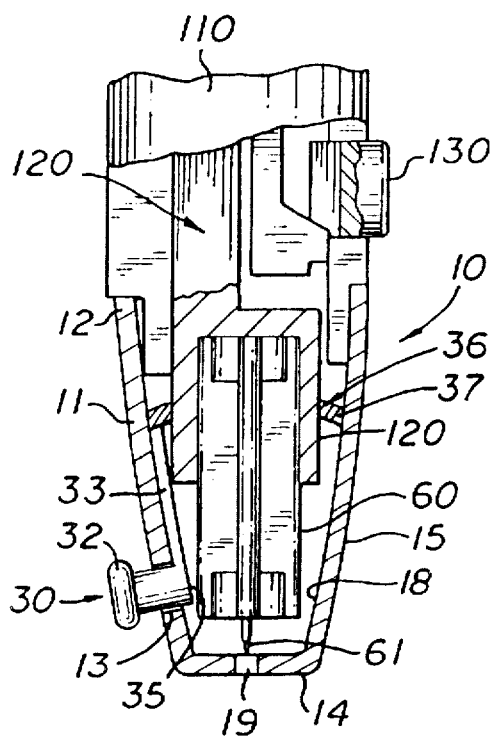
FIG. 6-B
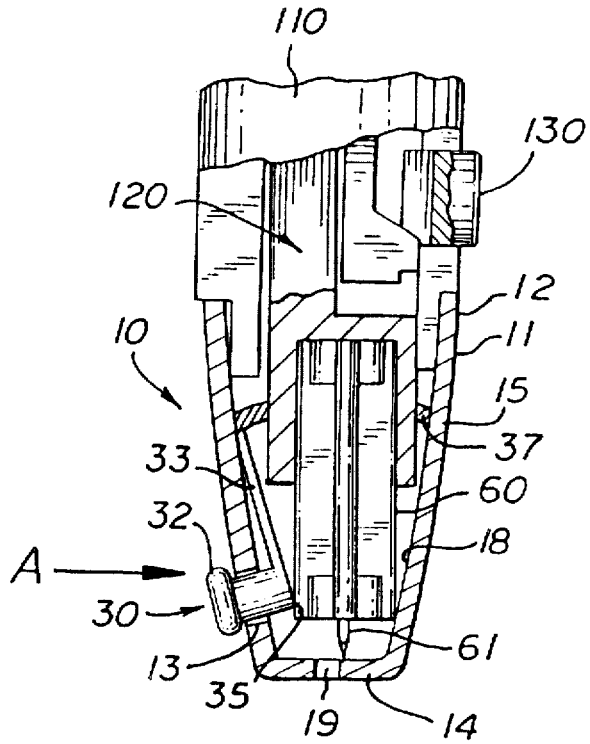
FIG. 7-A
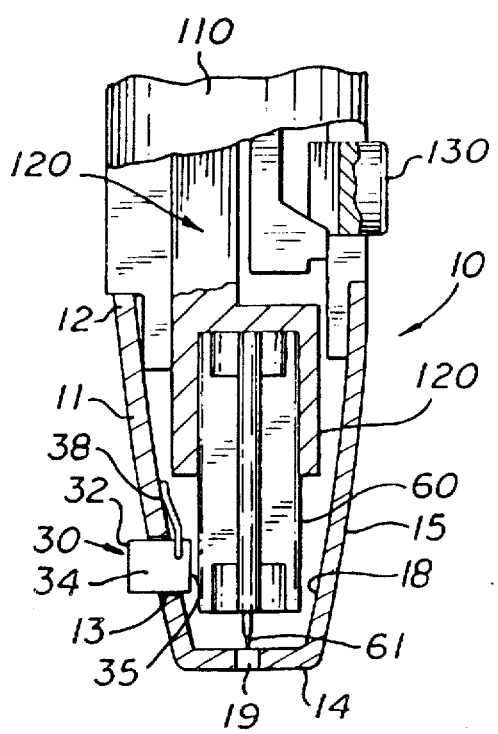
FIG. 7-B
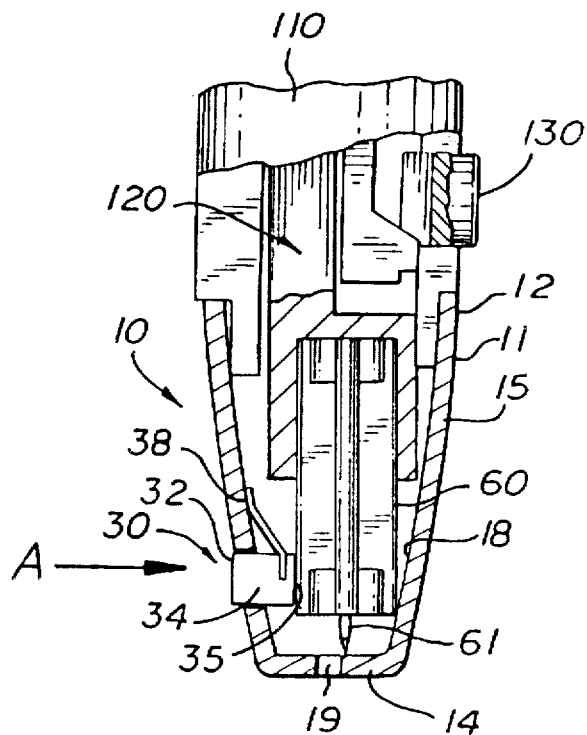

RE-USABLE END CAP FOR RE-USABLE LANCET DEVICES FOR REMOVING AND DISPOSING OF A CONTAMINATED LANCET

BACKGROUND OF THE INVENTION

1. Field of the Invention

The present invention relates generally to an end cap for re-usable lancet devices. More specifically, the present invention relates to an improved, re-usable end cap which is structured and disposed to permit a user to remove a contaminated lancet from a lancet device without directly contacting the contaminated lancet and further, to release the contaminated lancet into a proper disposal container.

2. Description of the Related Art

Lancets have long been employed to pierce or prick a patient's skin to provide a small outflow of blood that can be used in various medical tests. For example, diabetic patients typically need to have their blood tested periodically through-out the day to determine blood sugar levels, and frequently use lancets to draw blood for testing. A common type of lancet for drawing a small outflow of blood was described in expired U.S. Pat. No. 3,358,659 to Higgins. That patent generally teaches a lancet comprised of an elongated metal rod with a sharp sterile tip, a plastic retainer member molded directly about the lancet and from which the sharp tip extends outwardly, and a removable cap member connected to the plastic retainer member and in which the sterile tip is encased to prevent contamination prior to use.

Lancets are used both at home by patients and in medical offices or hospitals by health care professionals, and can be used to prick a patient's skin by manual penetration. More frequently, however, lancets are used in conjunction with a mechanical device, often referred to as a hand-held lancet device, into which the lancet is installed. Most of these devices employ a spring loaded mechanism which when activated, drives the lancet quickly and easily into a patient's skin, piercing it without much pain, so that blood can be let for testing. Lancets of the type described in the expired patent to Higgins are highly common and are suitable for use in hand-held lancet devices. It is understood of course, that once a lancet has been used to draw blood, it is contaminated, and should be removed from the lancet device and replaced with a sterile lancet for the next use.

In the home setting, patients use lancets in combination with hand-held lancet devices that are typically re-usable. For instance, it is in fact, common for manufacturers of glucose meters, which are used by diabetics, to include a re-usable lancet device with the sale of a glucose meter. In stark contrast, however, in the hospital and medical office setting, single use lancet devices are used, which are used only one time and then disposed of. This avoids the necessity of performing several steps that would be required if a re-useable lancet device were used to draw blood from a patient, namely, removing the contaminated lancet from the device, sterilizing the device after each use, and inserting a sterile lancet into the device for use on the next patient. These steps are requisite because after a lancet has been used to prick a patient's skin, the sharp lancet tip is contaminated with the patient's blood, skin or other bodily fluids. Similarly, the front end of the lancet device itself may also be viewed as contaminated in that it contacts the patient's skin and may have come into contact with some of the patient's blood or other bodily fluid. Given that there are various high-risk and life threatening diseases prevalent today throughout the world, many of which are transferable via contact with an infected person's blood or other bodily fluids, coming into contact with another person's blood and/or bodily fluids can pose an extremely hazardous health risk. This is absolutely true in the case where one directly contacts another's blood or other bodily fluid but also in the case where one indirectly contacts it, for example, by way of being accidentally jabbed with a contaminated needle or a contaminated lancet tip. To minimize the latter risk, hospitals and medical offices usually utilize single use lancets.

In the home setting where re-useable devices are common, however, the risk of being jabbed by a contaminated lancet is still present. Typically, this risk afflicts the care-givers of a patient or visiting health care attendants. As used lancets constitute an extremely hazardous form of waste, however, any one who may subsequently come into contact with contaminated lancets are also affected.

It should therefore be viewed as essential that contaminated lancet tips be safely shielded for proper disposal in order to prevent others from being accidentally jabbed. In achieving this, a first fundamental problem exists, namely, how to handle a contaminated lancet so as to remove it from a lancet device, without being jabbed. Known, re-useable and hand held lancet devices typically require some direct human contact with a contaminated lancet in order to remove it from the device. More specifically, presently available lancet devices require that the lancet be inserted into a lancet receiving assembly, that the lancet receiving assembly be set or loaded, and then activated or fired so as to pierce a patient's skin. Once the lancet has pierced the skin and a blood sample taken from the finger or other body part, the lancet is ready for removal from the lancet receiving assembly of the lancet device. At this point, however, some direct human contact with the contaminated lancet is generally required in order to do so, which is typically accomplished by grasping the body of the contaminated lancet with the thumb and index finger and pulling on it so as to slide the lancet out of the spring loaded mechanism (referred to herein as the lancet receiving assembly) of the device, whereupon the contaminated lancet may then be disposed of. Unfortunately, the sharp, contaminated tip of the lancet is almost always exposed during this maneuver, and the simple truth is that it is impossible for patients, their care givers and/or a visiting health care attendant to use extreme caution each and every time a contaminated lancet is handled. As a result, any person from any one of these groups may become jabbed by the sharp contaminated tip of the lancet in trying to remove it from the lancet device. The possibility of being infected with a life-threatening disease is ever present. Even if a care giver or other health care attendant were to wear latex gloves, as many health care workers do in modern times, the peril persists as the sharp tip of a contaminated lancet can effortlessly pierce through latex material and into the skin below it.

Even assuming that a contaminated lancet were capable of being safely removed from a lancet device in each and every instance, a fundamental second problem exists. Specifically, the contaminated lancet typically requires additional handling in order to properly dispose of it. Some patients and health care attendants are accustomed to carrying contaminated lancets around in the palm of the hand until they reach a proper container for disposing of such hazardous waste. This conduct also carries substantial risk for being jabbed with the sharp, contaminated lancet tip. Specifically, the person handling a contaminated lancet may inadvertently bump into an object or be bumped into by another person and consequently, may either jab themselves with the contaminated lancet tip or drop the contaminated lancet. In the event of the latter, additional and unnecessary handling of a contaminated lancet is again needed before the contaminated lancet can be discarded into a proper container for disposal.

Accordingly, there remains a significant need in the art for an apparatus which greatly facilitates the removal of contaminated lancets from lancet devices. Any such apparatus should permit one to do so without having to directly contact any part of the contaminated lancet. It would be preferable if any such apparatus could be simultaneously used to assist with the disposal of the contaminated lancet so as to prevent the need for other direct handling of the contaminated lancet. Ideally, any such apparatus would be re-useable, and capable of functioning with known, highly common and inexpensive lancets, such as the type described in the expired Higgins patent, and further, would also ideally be capable of functioning with commonly known, re-useable, hand held lancet devices. The present invention is directed towards solving these needs which remain in the art.

SUMMARY OF THE INVENTION

The present invention relates to a re-useable cap for use with common, hand-held and re-usable lancet devices. Typically, such lancet devices include a main body and an actuatable lancet receiving assembly which is structured and disposed to temporarily hold a common type of lancet and to drive the lancet into a piercing orientation wherein a patient's skin is momentarily pricked to draw a small amount of blood.

The re-useable cap of the present invention is seen to comprise a housing, which preferably has a partially open forward end, a more fully open back end and a surrounding sidewall structure between the ends defining a hollow interior within the housing. The back end of the re-useable cap is structured and disposed to be removably secured to the main body of the lancet device and the hollow interior of the cap is structured and disposed to permit movement of the lancet and lancet assembly therethrough and into the piercing orientation. In addition, the front end of the cap is structured and disposed to permit passage of preferably, just the sharp tip of the lancet therethrough upon movement of the lancet and lancet receiving assembly into the piercing orientation in order to effect the piercing of a patient's skin. The re-useable end cap of the present invention additionally comprises engagement means either formed directly on the housing of the end cap or attached thereto. The engagement means of the present invention are structured and disposed for movement between a first, withdrawn position and a second, engaged position upon activation by a user. In the second, engaged position, the engagement means are structured and disposed to engage the lancet and, upon removal of the end cap from the main body of the lancet device, to withdraw the lancet from the lancet receiving assembly. The engagement means of the present invention are also preferably structured and disposed to retain the contaminated lancet within the end cap until activated by a user for selectively releasing the lancet into a proper disposal container.

A primary object of the present invention is to provide a device which eliminates the need for patients, care givers, and health care attendants to directly contact any part of a contaminated lancet in order to remove it from a common, hand held and re-useable lancet device.

It is also a primary object of the present invention to provide a device which simultaneously permits the contaminated lancet to be properly disposed of, also without the need for direct contact with the contaminated lancet.

An object of the present invention is to provide a device which can be readily used in conjunction with common and presently available hand held lancet devices, as well as with lancet devices that may become known in the future.

It is also an object of the present invention to provide a device which can readily be used in conjunction with known, highly common and inexpensive lancets.

Yet another object of the present invention is to provide an end cap which both accomplishes the foregoing objectives and further, which is re-useable, primarily for the home setting.

These and other objects, features and advantages of the present invention will become more apparent from the following detailed description and accompanying drawings, in which:

BRIEF DESCRIPTION OF THE DRAWINGS

For a fuller understanding of the nature of the present invention, reference should be had to the following detailed description taken in connection with the accompanying drawings in which:

FIG. 1 is a an exploded perspective view of one type of a hand held lancet device and end cap.

FIG. 2 is also an exploded, partial perspective view of the lancet device illustrated in FIG. 1, with the end cap removed, and depicting a typical lancet and lancet cap member.

FIG. 3 is a an exploded perspective view of the hand held lancet device depicted in FIG. 1 and of one embodiment of the re-useable end cap of the present invention.

FIG. 4 is a bottom plan view of the re-useable end cap of the present invention.

FIG. 5-A is a cross sectional view of the re-useable end cap according to the present invention, illustrating a preferred embodiment of the engagement means in a first withdrawn position.

FIG. 5-B is also a cross-sectional view of the re-useable end cap illustrated in FIG. 5-A, but depicting the engagement means in a second engaged position.

FIG. 6-A is a cross sectional view of the re-useable end cap illustrating a more preferred embodiment of the engagement means in a first withdrawn position.

FIG. 6-B is also a cross-sectional view of the re-useable end cap illustrated in FIG. 6-A, but depicting the engagement means in a second engaged position.

FIG. 7-A is a cross sectional view of the re-useable end cap illustrating another embodiment of the engagement means in a first withdrawn position.

FIG. 7-B is also a cross-sectional view of the re-useable end cap illustrated in FIG. 7-A, but depicting the engagement means in a second engaged position. Like reference numerals refer to like parts throughout the several views of the drawings.

DETAILED DESCRIPTION OF THE PREFERRED EMBODIMENT

As seen in FIGS. 3 through 7-B, the present invention is directed towards an improved, re-useable end cap and is generally indicated as 10. The re-useable end cap, 10 is intended for use with re-useable, hand held lancet devices, such as that illustrated in FIGS. 1 and 2, indicated generally as 100. A brief discussion of the features of such lancet devices, 100, is warranted to appreciate the environment in which the present invention works.

The lancet device, 100, is seen to comprise a main body, 110 that is essentially a structure for housing a lancet receiving assembly, 120, a cocking mechanism (not shown) and trigger means, 130. The lancet receiving assembly 120 is structured and disposed to be movable within the housing or main body 110 and relative thereto. Specifically, the lancet receiving assembly 120 is structured and disposed to move from an intermediate, at-rest orientation, into a cocked orientation, and upon firing by trigger means 130, into a fully extended, piercing orientation, whereupon it automatically returns to the intermediate at-rest orientation. A cap, 140, is placeable over one end of the lancet main body 110, such as at 115. Device cap 140 is seen to have an open first end, 142 for sliding onto the main body of the lancet at 115, a partially open second end 144, and a skirt structure extending therebetween which defines a hollow interior 145.

The lancet receiving assembly 120 is additionally structured and disposed to removably receive a lancet, 60, therein, such as shown in FIG. 2. The lancet 60 is generally a tubular shaped member having cross shaped ridges 65 and contains an elongated metal rod with an exposed, sharp sterile tip 61. It is common for lancets such as lancet 60, to be packaged with a removable cap member 62, connected to the lancet 60 and in which the sterile tip is encased, to prevent contamination prior to use. In any event, lancet 60 is insertable into the lancet receiving assembly 120, whereupon, the lancet receiving assembly 120 may be pushed in the direction of end 117 within lancet body 110 so as to cock the assembly. At this point, and preferably before, cap member 62 can be twisted off and removed so as to expose the sharp sterile lancet tip 61 and further, the device cap 140 can now be placed on the lancet body 110. Also at this point, the device is ready for use to let a sample of blood from a patient and can be placed onto a patient's finger or other body part, with for example, end 144 of the cap 140 touching the skin. It will be appreciated that trigger means 130 are utilized to fire the lancet receiving assembly 120 and to impart driving movement to it and it follows, the lancet 60 carried therein. It will also be appreciated that the lancet receiving assembly 120 and lancet 60 are permitted to pass through the hollow interior of cap 140, with the sharpened tip 61 of the lancet 60 being permitted to momentarily extend through the partially open end 144 of cap 140. As the sharpened tip 61 of the lancet 60 passes out of end 144 of the cap 140, it momentarily and swiftly pierces the patient's skin and lets blood. Thereupon, the lancet receiving assembly 120 and the lancet 60 carried therein, automatically return to the intermediate, at-rest orientation within body 110 and cap 140. At this point, the lancet tip 61 is contaminated and can be removed by taking the cap 140 off the device 110 and manually withdrawing the contaminated lancet from the assembly 120.

As has been described, until the present invention, removing the contaminated lancet from the lancet receiving assembly 120 has required great caution as an imminent danger exists that one will be inadvertently jabbed by the exposed and contaminated sharp lancet tip 61. Part of the problem lies in that in order to remove the contaminated lancet, a movement of at least one hand towards the exposed and sharp contaminated tip 61 has typically been required, which carries the potential for either a direct or indirect "collision" with the sharp and contaminated lancet tip. The present invention is designed to avoid this potential for collision, and is specifically adapted to drastically reduce, if not eliminate altogether, the imminent danger of being inadvertently jabbed by the exposed and contaminated lancet tip. More particularly, the present invention is designed to eliminate the need for directly contacting any part of the contaminated lancet either to remove it from the device 110 or to dispose of it. Against this background, the present invention will now be described.

The re-usable end cap 10 of the present invention is specifically structured to replace end cap 140 of the lancet device as illustrated in FIG. 1. Referring now to FIG. 3, the re-useable cap 10 is seen to comprise a housing 11 having a back end 12, a forward end 14 and a surrounding sidewall structure 15 extending therebetween and defining housing 11 as tubular and with a substantially hollow interior 16. In the preferred embodiment, the surrounding side wall structure 15 is tapered between ends 12, 14, and ideally, tapers from a wider diameter adjacent back end 12 to a narrower diameter adjacent front end 14, as illustrated in FIGS. 5-A through 7-B. The back end 12 of the cap 10 is structured and disposed to be removably secured to the main body 110 of the lancet device 100, and to achieve this purpose, is at least partially open. Preferably, however, back end 12 comprises an open mouth sized to snugly fit over and onto end 115 of the lancet body. The substantially hollow interior 16 of the cap 10 is sized, dimensioned and configured to permit movement of at least the lancet 60 therethrough and into the piercing orientation, although, preferably, the substantially hollow interior 16 includes additional axial clearance thereabout to accommodate any portion of the lancet receiving assembly 120 that may pass therethrough during firing. The front end 14 of the cap 10 is similarly structured and disposed to permit passage of at least a tip 61 of the lancet 60 therethrough upon movement of the lancet 60 and lancet receiving assembly 120 into the piercing orientation. Thus, the front end 14 of the cap 10 is at least partially open, although in the preferred embodiment, the front end 14 is substantially closed and includes a small opening, such as at 19, shown in FIG. 4, which is preferably sized to be slightly larger than the outer diameter of the sharp tip 61 and elongated metal rod of the lancet 60.

As a unique and novel feature, the re-useable cap 10 of the present invention additionally comprises engagement means 30. The engagement means 30 are capable of being activated to engage the lancet 60 and to withdraw it from the lancet receiving assembly 120, upon removal of the cap 10 from the main body 110 of the lancet device 100. The engagement means 30 are intended for use after the lancet receiving assembly 120, and lancet 60 carried therein, have been fired and have pierced a patient's skin so as to render the lancet 60 contaminated. As such, in the preferred embodiment, the engagement means 30 are disposed on the surrounding sidewall structure 15 of the cap 10 intermediate ends 12 and 14, although more preferably, nearer to end 14, so as to generally correspond the position of the lancet 60, within the cap 10, once the lancet receiving assembly 120 has returned to the intermediate at-rest orientation within body 110 and cap 10. In addition, the engagement means 30 are structured and disposed to be attached to the cap 10 and to be movable relative thereto. Specifically, the engagement means 30 are movable between a first withdrawn position as illustrated in FIGS. 5-A, 6-A and 7-A, and a second engaged position as illustrated in FIGS. 5-B, 6-B and 7-B. In the first withdrawn position, the engagement means 30 are structured and disposed to permit free movement of the lancet 60 and at least part of the lancet receiving assembly 120 as they move through the cap 10 and into and out of the piercing orientation. In the second engaged position, the engagement means 30 are structured and disposed to engage the lancet 60, preferably pressing the lancet 60 against an opposite interior wall surface 18 of the housing's surrounding side wall structure 15, and further, to maintain the lancet in that position so as to withdraw the lancet 60 from the lancet receiving assembly 120 upon removal of the cap 10 from the main body of the lancet device 110.

To achieve this, the engagement means 30 comprise at least one member including a head portion 32 and an abutment segment 35. Preferably, the head portion 32 is structured to protrude from and extend out of the common plane defined by the sidewall structure 15, see FIGS. 5-A, 6-A and 7-A, so as to be exteriorly actuated by a user. Preferably, the abutment segment 35 is structured and disposed to dwell within the substantially hollow interior 16 of the cap 10, generally adjacent the inner surface 18 of surrounding sidewall 15 when in the first withdrawn position. It has been described and it will be appreciated that in the first withdrawn position, the engagement means 30 generally, and the abutment segment 35 specifically, should not interfere with the movement of the lancet 60 and lancet receiving assembly 120 through the cap 10 as they move into the piercing orientation.

Accordingly, in a more preferred embodiment, the present invention also comprises biasing means 38. Preferably, the biasing means 38 are operably connected to the engagement means 30 and are structured and disposed to bias or urge the engagement means 30 into the first withdrawn position. The biasing means may comprise a separate member such as a spring or in the case of the engagement means 30 being formed of a suitably rigid plastic material, may comprise a sufficient elastic memory to return to the first withdrawn position. Regardless, the biasing force exerted by the biasing means 38 is structured and disposed to be easily overcome by activation of the engagement means 30, such as a pressing motion on the head portion 32, to permit movement of the engagement means 30 into the second withdrawn position.

It will be appreciated that the engagement means 30 may be attached to the housing 11 of cap 10, in a number of ways, as will now be described. Preferably, the engagement means 30 are operably connected to the housing 11 of the cap 10, although the engagement means 30 may be directly formed on the housing 11 or may be operably coupled thereto, as well. Referring now to FIGS. 5-A and 5-B, the engagement means 30 are seen to comprise a single member 31, ideally in the form of a living hinge structure or a leaf spring structure formed on or out of the surrounding sidewall structure 15 of the housing 11. In this embodiment, the head portion 32 may be formed to have a series of ridges or grooves thereon to provide a convenient gripping surface for activating and moving the engagement means 30 from the first withdrawn position depicted in FIG. 5-A and into the second engaged position, illustrated in FIG. 5-B. It will be appreciated from these illustrations that the engagement means 30 may alternatively comprise a plurality of members, such as a pair of movable hinged members attached to the surrounding sidewall structure 15 of the housing 11 generally opposite each other. In that case, each member of the pair would be movable inwardly and towards the other so as to grasp the body of the contaminated lancet 60 therebetween in the second engaged position.

In a preferred embodiment, however, the engagement means will be operably connected to the cap 10, as is illustrated in FIGS. 6-A and 6-B. In this embodiment, the surrounding sidewall structure 15 of the end cap 10 includes an aperture 13 therein and into which the engagement means 30 are slidably inserted and maintained. As illustrated in FIGS. 6-A and 6-B, the engagement means 30 may comprise for example, an elongate member 33 having the head portion 32 and abutment segment 35 disposed at a first end and an anchor member 36 disposed at a, second end. In this embodiment, the head portion 32 of elongate member 33 is sized and structured to extend through and to protrude out of the aperture 13 of the cap 10 and further, the main body of the elongate member extends within the hollow interior 16, generally adjacent the interior surface 18 of surrounding sidewall structure 15, to the anchor member 36. Also in this embodiment, the anchor member 36 is in the form of a collar 37 which is sized and structured to be disposed within and to extend about the interior wall surface 18 of surrounding sidewall structure 15 of the cap, generally adjacent its open end 12, and may be adhesively or other wise attached thereto. In a similar but alternative embodiment, the collar may be sized and structured to be disposed about an exterior of the cap, i.e., about the surrounding sidewall structure 15, generally adjacent open end 12, with the main body of the elongate member 33 also extending downwardly along the exterior wall surface of cap 10 and with the abutment segment 35 being sized to extend through aperture 13 and to protrude slightly therefrom. In either of these embodiments, in the first withdrawn position the abutment segment 35 dwells within the substantially hollow interior 16 of the cap 10 generally adjacent the inner surface 18 of the surrounding sidewall structure 15 of cap 10.

It will be appreciated that the engagement means 30 could comprise other structural members and yet achieve the intended result of the invention. For example, the engagement means 30 may comprise a single button member 34 which extends through aperture 13 formed in the surrounding sidewall structure 15 of the cap 10 as illustrated in FIGS. 7-A and 7-B. In this embodiment, the button member 34 preferably has a head portion 32 defined at a first end, an abutment segment 35 defined at a second end thereof, and a main body extending between the ends which is slidably disposed and extends within the aperture 13 formed on the housing 11. The head portion 32 and abutment segment 35 are both structured and disposed to have an outer diameter which is larger than that of the aperture 13 in housing 11 so as to prevent the button member 34 from becoming dislodged or separated from the housing 11. Preferably, the button member 34 also includes biasing means 38 operably connected thereto to urge the button member 34 into the first withdrawn position, shown in FIG. 7-A, until such time as activation occurs to cause movement into the second engaged position, shown in FIG. 7-B. As another example, the housing 11 of the cap 10 may be formed to define an elongate slot 39 within surrounding side wall structure 15, structured and disposed to receive engagement means 30 comprising a wedge shaped member which is slidably received by and insertable within the elongate slot 39 of the housing 11. In such an embodiment, the main body of the wedge shaped member would be disposed in the first withdrawn position to not interfere with the movement of the lancet receiving assembly 120 and lancet 60 carried therein, but could be activated to move into the second engaged position with a nose and a portion of its main body engaging the lancet 60 within the cap 10, so as to withdraw the lancet from the lancet receiving assembly 120 upon removal of the cap 10 from the device 110. As yet other examples, the interior wall surface of the cap 10 could be formed to include small platform structure for holding and permitting movement of the engagement means 30 between the first withdrawn and second engaged positions or could even utilize a momentary clutch member.

The engagement means 30 are seen in any case to be moveable between the first withdrawn position and the second engaged position and share certain features in common. Referring now to FIGS. 5-A, 6-A and 7-A, in the first withdrawn position the engagement means 30 are structured and disposed to permit free movement of the lancet 60 and at least part of the lancet receiving assembly 120 as they move through the cap 10 and into and out of the piercing orientation. Accordingly, the abutment segment 35 of the engagement means 30 is seen to dwell within the substantially hollow interior of cap 10, closely adjacent side wall 15, as is any structure operably connected to abutment segment 35 and similarly situated within the interior of cap 10. Referring now to FIGS. 5-B, 6-B and 7-B, in the second engaged position the engagement means 30 are structured and disposed to engage the lancet 60, preferably pressing the lancet 60 against an opposite interior wall surface 18 of the cap's surrounding side wall structure 15, and further, to maintain the lancet 60 in that position so as to effectively withdraw the lancet 60 from the lancet receiving assembly 120 upon removal of the cap 10 from the main body of the lancet device 110. Accordingly, the abutment segment 35 of the engagement means 30 is seen to have penetrated the substantially hollow interior of cap 10 and to have both contacted and engaged the lancet 60. To accomplish this, the head portion 32 has been activated by a user, pushing it in the direction of the arrow A, which urges the abutment segment 35 into the second engaged position wherein the body of the lancet 60 is engaged and upon continued pushing movement, pinned, against an opposite inner surface 18 of sidewall structure 15.

Finally, the engagement means 30 of the present invention are structured and disposed to permit a user to retain a contaminated lancet 60 within the hollow interior 16 of the cap 10 so as to facilitate proper disposal of the contaminated lancet 60. More specifically, the engagement means 30 are structured and disposed to permit a user to selectively maintain the engagement means 30 in the second engaged position, even after removing the contaminated lancet 60 from the lancet receiving assembly 120 of the device 110. As such, the user may continue to maintain the engagement means 30 in the second engaged position and while doing so, may maneuver the end cap 10 into position above a sharp box, commonly known in the industry for disposing of hazardous waste, and may then selectively release the engagement means 30, thereby permitting the contaminated lancet 60 to drop into the sharp box for proper disposal. Alternatively, upon removing a contaminated lancet 60 from a device 110 with cap 10, a user may instead choose to carry the end cap 10 like a cup, captivating the contaminated lancet therein, and may simply dump the contaminated lancet 60 into a sharp box or other container for proper disposal, without continuing to maintain the engagement means 30 in the second engaged position. At this point, the re-useable end cap 10 of the present invention is ready to be used again and may simply be re-attached to the re-useable, hand held lancet device 110, as at 115, until it is needed for use again.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,
what is claimed is:
1. An improved lancet device comprising:
I) a main body,
II) an actuatable lancet receiving assembly structured and disposed to temporarily hold a lancet and to drive the lancet into a piercing position, and III) a re-useable cap, said re-useable cap comprising:
  a) a substantially non-deformable housing having an at least partially open forward end and back end and a surrounding sidewall structure between said ends defining a hollow interior within said housing;
  b) said back end of said cap structured and disposed for being removably secured to the main body of the lancet device;
  c) said hollow interior of said cap structured and disposed to permit movement of the lancet therethrough and into the piercing position;
  d) said front end of said cap structured and disposed to permit passage of at least a tip of the lancet therethrough upon movement of the lancet and lancet receiving assembly into the piercing position;
  e) engagement means operably coupled to said cap and structured to be affirmatively actuated for engaging the lancet while said housing remains substantially undeformed so as to prevent relative movement between the lancet and said cap and thereby provide for withdrawing of the lancet from the lancet receiving assembly upon removal of said cap from the main body of the lancet device; and
  f) said engagement means further being capable of being actuated for selectively releasing the lancet for disposal.

2. An improved, lancet device as recited in claim 1, wherein said engagement means are movable relative to said cap between a first withdrawn position and a second engaged position.

3. An improved, lancet device as recited in claim 2, wherein said cap includes biasing means operably coupled to said engagement means for biasing said engagement means towards said first, withdrawn position.

4. An improved, lancet device as recited in claim 3, wherein said engagement means comprise at least one member and include a head portion and an abutment segment.

5. An improved, lancet device as recited in claim 3, wherein said engagement means return to said first withdrawn position upon being released.

6. An improved lancet device as recited in claim 1, wherein said engagement means are disposed on said cap between said first and second ends and are aligned with a location of the lancet when the lancet receiving assembly is in an intermediate at-rest orientation.

7. An improved, lancet device as recited in claim 1, wherein said engagement means are exteriorly actuatable by a user.

8. A lancet device comprising:
I) a main body;
II) an actuatable lancet receiving assembly structured and disposed to temporarily hold a lancet and to drive the lancet into a piercing position;
III) a re-useable cap, said re-useable cap comprising:
  a) a housing having an at least partially open forward end and back end and a surrounding sidewall structure between said ends defining a hollow interior within said housing;
  b) said back end of said cap structured and disposed for being removably secured to the main body of the lancet device;
  C) said hollow interior of said cap structured and disposed to permit movement of the lancet therethrough and into the piercing position;
  d) said front end of said cap structured and disposed to permit passage of at least a tip of the lancet therethrough upon movement of the lancet and lancet receiving assembly into the piercing position; and e) engagement means attached to said cap and structured and disposed to be movable relative to said cap between a first withdrawn position and a second engaged position, said engagement means in said second engaged position engaging the lancet while said housing remains substantially undeformed and preventing relative movement between the lancet and said cap upon removal of said cap from said main body so as to withdraw the lancet from a retained position in said actuatable lancet receiving assembly.

9. An improved, lancet device as recited in claim 8, wherein said engagement means are structured and disposed to permit free movement of the lancet and at least part of the lancet receiving assembly through said cap and into the piercing position, when said engagement means are disposed in said first withdrawn position.

10. An improved, lancet device as recited in claim 9, wherein said cap includes biasing means operably coupled to said engagement means, said biasing means being structured and disposed for biasing and returning said engagement means into said first, withdrawn position, upon said engagement means being released from said second engaged position.

11. An improved, lancet device as recited in claim 9, wherein said engagement means are structured and disposed to be selectively moved into said second engaged position wherein said means engage the lancet.

12. An improved, lancet device as recited in claim 11, wherein said engagement means are structured and disposed to withdraw the lancet from the lancet receiving assembly upon removal of said cap from the main body of the lancet device when disposed in said second position.

13. An improved, lancet device as recited in claim 12 wherein said engagement means includes a head portion and an abutment segment.

14. An improved, lancet device as recited in claim 13, wherein said head portion of said engagement means is structured and disposed to protrude from and extend out of a common plane defined by said sidewall structure of said cap so as to be exteriorly actuated by a user.

15. An improved, lancet device as recited in claim 13, wherein in said second engaged position, said abutment segment is structured to pin the body of the lancet against an inner surface of said surrounding side wall structure so as to hold and withdraw the lancet from the lancet receiving assembly upon removal of said cap from the lancet device.

16. A device comprising:

a) lancet holding means;

b) a lancet inserted into said holding means; and c) a cap having a first end comprising an open mouth for removable attachment to said lancet holding means, a second end having an opening therein and a hollow, main body between said ends, said main body being formed of a generally non-deformable material;

d) said open mouth and main body of said cap structured and disposed to permit at least partial passage of said lancet and lancet holding means therethrough and into a piercing position wherein a sharp tip of said lancet is exposed through said opening of said second cap end; and e) engagement means formed on said cap, exteriorly actuatable, and movable relative to said cap between a first withdrawn position and a second engaged position wherein the lancet is engaged and can be withdrawn from said lancet holding means and selectively retained within said cap said main body remaining substantially undeformed while said engagement means moves from said first position to said second position.

17. An improved, re-useable lancet cap for a lancet device as recited in claim 16, wherein said engagement means comprise at least one member.

18. An improved, re-useable lancet cap for a lancet device as recited in claim 17 further comprising biasing means operably coupled to said engagement means for biasing and returning said engagement means into said first withdrawn position upon said engagement means being selectively released from said second engaged position.

19. An improved, re-useable lancet cap for a lancet device as recited in claim 18 wherein said engagement means include a head portion and an abutment segment, said head portion being exteriorly actuatable for selectively causing movement of said engagement means into said second engaged position.

20. An improved, re-useable lancet cap for a lancet device as recited in claim 19 wherein said engagement means comprises a single member and said abutment segment is structured and disposed to be selectively moved into an interior of said housing and into said second engaged position wherein said abutment segment engages the body of the lancet and pins the lancet against an inner surface of said surrounding sidewall structure of said cap, so as to hold and withdraw the lancet from the lancet receiving assembly of the lancet device upon removal of said cap from the lancet device.

* * * * *